United States Patent [19]

Vrieland et al.

[11] 3,957,897

[45] May 18, 1976

[54] METHOD OF OXYDEHYDROGENATION OF ALKYL AROMATIC COMPOUNDS

[75] Inventors: G. Edwin Vrieland, Midland, Mich.; Hans R. Friedli, Lake Jackson, Tex.

[73] Assignee: The Dow Chemical Company, Midland, Mich.

[22] Filed: May 28, 1974

[21] Appl. No.: 473,622

[52] U.S. Cl. .................... 260/699 R; 260/624 B; 260/650 R
[51] Int. Cl.² ........................................ C07C 5/48
[58] Field of Search ........ 260/669 R, 680 E, 290 V, 260/650 R, 329 R, 624 B; 252/437

[56] References Cited
UNITED STATES PATENTS

| | | | |
|---|---|---|---|
| 3,149,082 | 9/1964 | Bowman et al. | 252/437 |
| 3,409,696 | 11/1968 | Minnis et al. | 260/680 E |
| 3,451,945 | 6/1969 | Eden | 252/437 |
| 3,541,172 | 11/1970 | Stowe et al. | 260/669 R |
| 3,733,327 | 5/1973 | Vrieland et al. | 260/290 V |
| 3,781,222 | 12/1973 | Weisang et al. | 252/437 |

OTHER PUBLICATIONS

Kirk–Othmer, Encyclopedia of Chemical Technology, 2nd Ed., (1969), pub. by Interscience, Vol. 20, pp. 219–222 and 226.

Primary Examiner—Paul M. Coughlan, Jr.
Attorney, Agent, or Firm—Stephen Hoynak; Glwynn R. Baker

[57] ABSTRACT

Certain alkaline earth pyrophosphates, such as Ca, Mg, and Sr pyrophosphates are superior catalysts for oxydehydrogenating alkyl aromatic compounds including nitrogen heterocyclics which have at least one $C_2$-$C_6$ alkyl side chain to form derivatives having side chain unsaturation. The alkyl aromatic compound can have 1-2 rings. The process is carried out at 450°–650°C. and a space velocity of 55–2500.

14 Claims, No Drawings

METHOD OF OXYDEHYDROGENATION OF ALKYL AROMATIC COMPOUNDS

BACKGROUND OF THE INVENTION

Certain alkaline earth-nickel phosphates, such as calcium-nickel phosphate or strontium-nickel phosphate are good dehydrogenation catalysts for converting n-butenes to butadiene or for oxydehydrogenating lower aliphatic alkanes and alkenes to dienes. Although they also dehydrogenate alkyl aromatic hydrocarbons to their alkene aromatic derivatives, these catalysts are not as active for this purpose, as are the well-known self-regenerative catalysts containing iron, zinc or magnesium oxides and potassium oxide or a potassium compound convertible to the oxide. Calcium, magnesium or strontium ortho-phosphates, however, are not good catalysts for dehydrogenating either butenes or alkyl aromatic hydrocarbons.

One of the shortcomings of the self-regenerative dehydrogenation catalysts for converting ethylbenzene to styrene is that under acceptable commercially operating conditions the conversion of the ethylbenzene is in the 35–40% range. Selectivity, however, is in the 85–95% range. The self-regenerative catalysts are not sufficiently selective in oxydehydrogenation systems to be useful commercially for converting alkyl benzenes to alkene derivatives in the presence of oxygen.

Therefore, an object of this invention is the provision of a superior catalyst for oxydehydrogenation of an alkyl aromatic compound. Another object is to provide a process for oxydehydrogenating alkyl aromatic compounds in which process superior conversions with high selectivities of the alkyl group to an alkene group are obtained.

SUMMARY OF THE INVENTION

This invention concerns novel catalysts and a method of oxydehydrogenating alkyl aromatic compounds having at least one $C_2-C_6$ alkyl group, including nitrogen heterocyclics, and 1-2 rings in the aromatic moiety, to form derivatives having aliphatic unsaturation in the side chain. More particularly, the catalysts are calcium, magnesium or strontium pyrophosphates. The method comprises passing a mixture of an oxygen containing gas, and vapors of the alkyl aromatic compounds, with or without an inert diluent vapor, at least one of the catalysts or a mixture of such catalysts at a temperature of from about 450° to about 650°C., at a space velocity of from about 55 to about 2500.

DETAILED DESCRIPTION OF THE INVENTION

2MHPO pyrophosphate catalysts of this invention can be prepared by dehydrating the corresponding Ca, Mg, or Sr mono-hydrogen phosphates in accordance with the following:

In the above equation M is Ca, Mg or Sr, and X is 0–2. Preferably the dihydrate is used for this catalyst preparative method.

Another means for preparing pyrophosphates is to heat the alkaline earth mono-ammonium phosphate and split out $H_2O$ and $NH_3$. This process is characterized by the following formula:

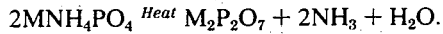

The third procedure for preparing the catalyst is to react a water soluble Ca, Mg or Sr salt with $NH_4H_2PO_4$, $(NH_4)_2HPO_4$ or $H_3PO_4$. The amount of the mono or diammonium phosphate or phosphoric acid should be in excess of that needed to form the orthophosphate and at least sufficient to form the pyrophosphate. The precipitate which forms in the reaction is filtered, dried and calcined. In this procedure the $PO_4^{3-}$/alkali metal ratio should preferably be less than 2. One $Ca_2P_2O_7$ prepared by heating $CaHPO_4.2H_2O$ (Mallinckrodt) at 500°C. for 4hours. The catalyst was then crushed and the 8 to 20 mesh portion was used.

Another $Ca_2P_2O_7$ catalyst was prepared by neutralizing a 2.2 molar aqueous solution of $(NH_4)_2HPO_4$ with ammonia. To 250 cc of the neutralized solution were added 250 cc of 1.2 1.2 molar aqueous solution of $Ca(NO_3)_2.4H_2O$ in a Waring blender, while stirring rapidly. The precipitate was filtered, dried, pressed and calcined at 550°C. for 4 hours. The catalyst was crushed and sieved. The 8 to 20 mesh particles were used for the examples herein.

A $Mg_2P_2O_7$ catalyst was prepared by heating $MgNH_4PO_4$ to 550°C. The catalyst was thereafter crushed and sieved. The particles of 8 to 20 mesh were used in the examples.

The $Sr_2P_2O_7$ was prepared by following the procedure for making $Mg_2P_2O_7$.

The molar ratio of oxygen to alkyl aromatic compound fed into the reactor can range from about 0.5 to about 4.0 moles of $O_2$ per mole of alkyl aromatic compound, but a preferred range is from about 0.5 to about 1.5 and most preferred is a range of about 0.9 to about 1.1 moles $O_2$ per mole of aromatic compound.

The oxygen can be pure oxygen air or air enriched with oxygen.

The space velocity (vol./vol./hr.) can range from about 55 to 2500, but a preferred range is from about 250 to about 800 Most preferred is a range of from about 800 to about 1800.

Diluents when used can be the noble gases, nitrogen, carbon dioxide or steam. These can range from about 4–16 volumes per volume of alkyl aromatic compound, but preferably range from about 4 to about 11 volumes.

The pressure at which the reaction can be run ranges from 0.5 to about 5 atmospheres, but it is preferable to operate at autogenous pressure which is generally the range of about 1 to about 2 atmospheres.

The reaction can be effected in a temperature range of from about 450° to about 650°C., but a preferred range is from about 500° to about 650°C.

Care should be exercised to avoid explosive mixtures when feeding the alkyl aromatic compound and oxygen into the reactor.

The examples which follow are intended to illustrate, but not to limit the invention. All parts are by volume unless specifically indicated otherwise.

Unless otherwise indicated the reactor for this and subsequent examples was a high silica glas tube 15 mm I.D. and 42 cm. long, with an inlet for the compound to be dehydrogenated and another for a premixed feed of oxygen and an inert diluent. After loading the reactor with catalyst, coarse, high silica chips were placed above the catalyst layer to serve as a mixing and preheating area. The reactor was heated by placing it in an electric resistance furnace.

The reactor was loaded with 20 ml. of the pyrophosphate, and then high silica chips were loaded on top of the catalyst.

A feed of 6:1;1 ratio of inert gas, oxygen and ethylbenzene, respectively, at a GHSV of 360 hr.$^{-1}$ was used unless otherwise specified.

Typically about 10 cc per minute of alkyl aromatic vapor, 10–15 cc per minute of oxygen, and 90 cc per minute of nitrogen per minute flowed through the reactor.

The effluent line from the reactor had a valve to divert a portion of the flow to an automated vapor phase chromatograph for analyzing $O_2$, $N_2$, CO, and $CO_2$ in one chromatographic system and hydrocarbons (benzene, toluene, alkyl benzenes) with 2 or more carbon atoms and the corresponding alkenyl benzene.

The aromatic hydrocarbons were separated in a column containing carbowax 20 M plus 2% KOH on Chromasorb P (60–80 M).

EXAMPLE 1

The catalyst in this instance was made by converting $CaHPO_4.2H_2O$ to $\beta\text{-}Ca_2P_2O_7$ by calcining at 550°C. The diluent or inert gas was helium and the reaction temperature was 525°–530°C. Ethyl benzene was the aromatic hydrocarbon in the feed. The catalyst had a surface area of 7.5 sq. m. per g.

The conversion of ethylbenzene was 65.4% and of oxygen 91.9% The selectivity to styrene was 92.0% to CO 4.1% and to $CO_2$ 3.9%

EXAMPLE 2

The procedure of Example 1 was repeated on the same reaction mixture, using a catalyst that was prepared by reacting $Ca(NO_3)_2$ with an excess of ammonia neutralized $(NH_4)_2HPO_4$ by the steps described above for making $\beta\text{-}Ca_2P_2O_7$. The conversion of ethylbenzene in this run was 67.4% and that of oxygen 95.3%. The selectivity to styrene was 94.5%, to CO 4.5% and $CO_2$ 3.1%.

EXAMPLE 3

The process of Example 1 with the reaction mixture there described was run using a catalyst made by mixing $Ca(NO)_2$ with 2 molar equivalents of $(NH_4)_2HPO_4$ and calcining the precipitate to form $Ca_2P_2O_7$. This catalyst had a surface area of 9.1 meters per gram.

In this run 58.2% of the ethylbenzene and 100% of the oxygen were converted. The selectivity to styrene was 87.6%, to CO 4.9%, and to $CO_2$ 7.6%.

EXAMPLES 4–7

The catalysts in this series were made in accordance with the following equation.

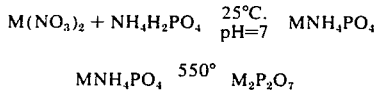

The feed contained helium oxygen and ethylbenzene in a molar ratio of 6:1:1, respectively. The GHSV was 360 $hr.^{-1}$ and the temperature was 527°–532°C.

Tabulated below are the results obtained in those runs.

| Ex. | Catalyst | Surface Area ($m^2/g$) | % Conversion | | % Selectivity | | |
|---|---|---|---|---|---|---|---|
| | | | E.B. | $O_2$ | Sty. | CO | $CO_2$ |
| 4 | $Mg_2P_2O_7$ | 35.4 | 70.5 | 100 | 92.8 | 2.8 | 4.4 |
| 5 | $Mg_2P_2O_7$ | | 75.2 | 100 | 90.9 | 4.2 | 5.0 |
| 6 | $Ca_2P_2O_7$ | 6.2 | 67.4 | 95.3 | 92.5 | 4.5 | 3.1 |
| 7 | $Sr_2P_2O_7$ | 2 | 63.9 | 89.0 | 90.7 | 4.1 | 5.2 |

E.B. = ethyl benzene
Sty. = styrene

For comparative purposes a $Ba_2P_2O_7$ catalyst made by the procedure described in this example, showed a conversion of ethyl benzene of 28.5% and $O_2$ of 40.3%. The selectivity to styrene was 92.6%.

In other comparative tests calcium meta-phosphate $Ca(PO_3)_2$ converted only 0.4% of the ethylbenzene and calcium apatite converted 41.2% with a selectivity to styrene of only 76.3%.

Other alkyl aromatic compounds which can be dehydrogenated to the corresponding styrenes by the procedures of this invention include, but are not limited to, ethyl toluene, ethyl xylene, ethyl phenols, t-butyl ethyl benzene, and ring chlorinated or brominated ethyl benzene. Diethyl benzene is converted to a mixture of divinyl benzene and ethyl styrene. Ethyl pyridines are converted to vinyl pyridines, ethyl naphthalenes to vinyl naphthalenes and ethyl thiophenes to vinyl thiophene. Isopropyl benzene is converted to alpha methyl styrene.

We claim:

1. A method of dehydrogenating an alkyl aromatic compound, selected from the class consisting of ethyl benzene, ethyl toluene, t-butyl ethyl benzene, diethyl benzene, ring chlorinated or brominated ethyl benzene, ethyl naphthalene, ethyl phenol, and isopropyl benzene to form a derivative having aliphatic unsaturation in the side chain, comprising passing a mixture of said alkyl aromatic compound and an oxygen containing gas in a mole ratio of 0.5 to 4.0 moles oxygen per mole of alkyl aromatic compound, over at least one of calcium, magnesium or strontium pyrophosphate, at a temperature from about 450° to about 650°C.

2. The method of claim 1 in which the catalyst is calcium pyrophosphate.

3. The method of claim 1 in which the catalyst is magnesium pyrophosphate.

4. The method claim 1 in which the catalyst is strontium pyrophosphate.

5. The method of claim 2 in which a mixture of an inert diluent, oxygen and ethyl benzene in a mole ratio of 6:1:1, respectively, is passed over $\beta$-calcium pyrophosphate at a temperature of 525°–530°C.

6. The method of claim 2 in which a mixture of an inert diluent, oxygen and ethyl benzene in a mole ratio of 6:1:1, respectively, is passed over the magnesium pyrophosphate at a temperature of 527°–532°C.

7. The method of claim 1 in which a mixture of an inert diluent, oxygen and ethyl benzene is passed over strontium pyrophosphate catalyst at a temperature of 527°–532°C.

8. The method of claim 1 in which the temperature is from about 500° to about 650°C.

9. The method of claim 1 in which the space velocity is from about 250 to about 1800.

10. The method of claim 9 in which the space velocity is from about 800 to about 1800.

11. The method of claim 2 in which the alkyl aromatic compound is ethyl benzene.

12. The method of claim 3 in which the alkyl aromatic compound is ethyl benzene.

13. The method of claim 4 in which the alkyl aromatic compound is ethyl benzene.

14. The method of claim 1 in which the alkyl aromatic compound is ethyl naphthalene.

* * * * *

UNITED STATES PATENT AND TRADEMARK OFFICE
CERTIFICATE OF CORRECTION

PATENT NO. : 3,957,897
DATED : May 18, 1976
INVENTOR(S) : G. Edwin Vrieland & Hans R. Friedli It is certified that error appears in the above-identified patent and that said Letters Patent are hereby corrected as shown below:

Col. 1, line 54, delete "2MHPO" and insert -- The --.

Col. 1, line 59, in the formula, insert an arrow below the word "Heat", as $$\xrightarrow{\text{Heat}}$$

line 59, at the end of the formula, insert a period --.--

Col. 1, line 67, in the formula, insert an arrow below the word "Heat", as $$\xrightarrow{\text{Heat}}$$

Col. 2, line 15, delete "1.2", first occurrence, and insert --a--.

Col. 2, line 37, delete "800" and insert -- 1800. --.

Col. 2, line 57, delete "glas" and insert -- glass --.

Col. 2, line 68, delete "6:1;1" and insert -- 6:1:1 --.

Col. 3, in "Examples 4-7", in both formulas insert arrows as follows:

$$\xrightarrow[\text{pH=7}]{25°C.}$$

and $$\xrightarrow{550°}$$

Col. 4, in Claim 4 after "method" insert -- of --.

Signed and Sealed this

Thirtieth Day of November 1976

[SEAL]

Attest:

RUTH C. MASON
*Attesting Officer*

C. MARSHALL DANN
*Commissioner of Patents and Trademarks*